: US 7,432,949 B2
(45) Date of Patent: Oct. 7, 2008

(54) MOBILE VIDEOIMAGING, VIDEOCOMMUNICATION, VIDEO PRODUCTION (VCVP) SYSTEM

(76) Inventors: Christophe Remy, 2022 Evergreen St., Burbank, CA (US) 91505; Simon P. King, 130 Carroll Dr., Annapolis, MD (US) 21403

(*) Notice: Subject to any disclaimer, the term of this patent is extended or adjusted under 35 U.S.C. 154(b) by 680 days.

(21) Appl. No.: 10/922,597

(22) Filed: Aug. 20, 2004

(65) Prior Publication Data

US 2005/0052527 A1    Mar. 10, 2005

Related U.S. Application Data

(60) Provisional application No. 60/496,395, filed on Aug. 20, 2003.

(51) Int. Cl.
*H04N 7/14* (2006.01)
*A61B 5/00* (2006.01)

(52) U.S. Cl. ............... 348/14.02; 348/14.01; 348/14.08

(58) Field of Classification Search ... 348/14.01–14.09, 348/14.1, 14.11, 14.12; 600/300, 301; 606/130
See application file for complete search history.

(56) References Cited

U.S. PATENT DOCUMENTS 5,489,938 A * 2/1996 Maruyama et al. ....... 348/14.08
6,256,374 B1 * 7/2001 Tomasetti et al. .......... 378/98.2
6,848,842 B2 * 2/2005 Saruhashi .................... 396/428
6,906,741 B2 * 6/2005 Canova et al. ........... 348/14.08
7,068,575 B2 * 6/2006 Gabryjelski ............... 369/47.33
2001/0034530 A1 * 10/2001 Malackowski et al. ...... 606/130
2001/0048464 A1 * 12/2001 Barnett ..................... 348/14.08

FOREIGN PATENT DOCUMENTS

EP              998144 A2  *  5/2000

* cited by examiner

*Primary Examiner*—Melur Ramakrishnaiah
(74) *Attorney, Agent, or Firm*—Ober/Kaler; Royal W. Craig

(57) ABSTRACT

A mobile self-powered videoimaging, video communication, video production (VCVP) system designed specifically for health care industry that provides high-resolution audio, video and data communications, production and recording capabilities at hospital operating room/procedure room or field environments for transmission to other remote locations. The VCVP system generally comprises a mobile platform with a plurality of cameras, at least one being mounted on an extensible boom for overhead imaging of surgical procedures. An array of video production equipment is rack-mounted inside the platform, as is an array of network teleconferencing equipment. The mobile imaging system may be parked at a convenient location in an operating room or other environment and controlled by a single operator. As the surgery proceeds, the operator can multiplex the camera signals into a live high resolution video/audio feed that is networked in real time for teleconferencing, and/or recorded to a hard drive or in any known format such as Mini-DV, S-VHS, VHS and DVD as desired.

15 Claims, 9 Drawing Sheets

MOBILE VIDEOIMAGING, VIDEOCOMMUNICATION, VIDEO PRODUCTION (VCVP) SYSTEM

CROSS-REFERENCE TO RELATED APPLICATION(S)

The present application derives priority from U.S. provisional application Ser. No. 60/496,395, filed Aug. 20, 2003.

BACKGROUND OF THE INVENTION

1. Field of the Invention

The present invention relates to video imaging systems and, more specifically, to a mobile video imaging, video communication and video production (VCVP) system designed specifically for the health care industry that provides high-resolution interactive audio, video and data communications between hospital operating room/procedure room environments and other remote locations for education, consulting, surgical assistance, diagnostics, demonstrations, and the like.

2. Description of the Background

There are many geographic areas where rural physicians and health practitioners need continuing education, and possibly real-time guidance from experts in carrying out various surgical procedures, etc. Unfortunately, distance and limited resources make it increasingly complicated for providers to furnish these services. This is especially true for military medics who often need education or guidance on certain procedures in the field. The problem has prompted many efforts to provide education and or real-time assistance via videoconferencing and even remote robotic surgery. Unfortunately, these efforts piece together existing hardware and fail to offer a solution that is economical, productive and cost effective in the various situations which would benefit.

Situations calling for real-time assistance are quite apparent, for example, an army medic who needs to perform an unfamiliar procedure in the field. There are also numerous situations where video production services are required in a medical setting, including academic surgical procedural programs to be used in teaching students, or surgical procedural/ promotional programs for medical devices, instructional & assembly programs for mapping out the steps for assembling or using a complicated apparatus, seminar & workshop capture, patient education programs & documentary, sales force motivational programs, etc. Indeed, many surgeries are now broadcast by live event video production and internet broadcasting or satellite uplink. Both recorded program production as well as live event productions require extensive production overhead.

Unfortunately, the army medic has no ready solution. Medical production services are available, but usually in the form of a conventional video crew. The crew equip an operating room with video cameras, microphones, video switchers, audio mixers, both preview and viewing monitors, hundreds of feet of cables, and they record or broadcast the surgery. The work product of the various cameras and crewmen may be broadcast and recorded in real time or turned over to an editor for mixing, editing, to generate a final edited master recorded on tape/digital tape/CD/DVD, etc.

There have been few attempts to consolidate the process in the surgical setting to make it less obtrusive, more flexible in serving all the foregoing needs, and more economical to health care providers. One effort is described in United States Patent Application No. 20030142204 by Rus, Steven H. filed Jul. 31, 2003. This application discloses a surgical lighting control and video system that gives a user access to multiple devices at one station and makes control of the system simpler and more intuitive. A graphical LCD display is used to control a plurality of devices, such as overhead lighting, ambient lighting, cameras, and other operating room accessories. A voice interface allows the surgeon to adjust lighting and other aspects by simply speaking. A foot pedal interface and an infra-red remote control interface grant the surgeon control of the cameras, enabling direct control of rotate and zoom functions of the camera.

Surgeons generally are not capable or willing to attend to all of their own video video imaging, production and communications needs themselves while indisposed with a patient. A better solution would be a mobile video imaging, video communications and video production system capable of being manned by a single trained person. In the context of surgical imaging, such as system must provide high-resolution interactive audio, video and data communications between hospital operating room/procedure room environments and other remote locations for education, consulting, remote surgical assistance, diagnostics, demonstrations, and the like.

SUMMARY OF THE INVENTION

It is therefore an object of the present invention to provide a mobile video imaging, video communication, video production (VCVP) system designed specifically for health care and surgical video imaging and suitable for operation by a single trained person which provides a complete array of audio and high-resolution video capture tools, mixing and editing tools, recording capabilities to a variety of common analog and digital formats, and real time video and data communications capabilities for networked communications for teleconferencing between hospital operating room/procedure room environments and other remote locations for education, consulting, remote surgical assistance, diagnostics, demonstrations, and the like.

It is another object to provide a mobile VCVP system as described above which is contained in a portable base with fully articulating boom-mounted video camera for high-resolution close-up imaging in any health care arena (such as an operating room).

It is still another object to provide a mobile VCVP system as described above which includes an array of components to facilitate video switching, editing and production capabilities, plus an array of components to facilitate full networking and video communication capabilities, all enclosed in a self-powered portable cabinet.

It is still another object to provide a mobile VCVP system suitable for use in an operating room environment, and for porting between various locations in a hospital, with sealed fail-safe on board battery system.

In accordance with the foregoing objects, the present invention is a mobile communication and video production (VCVP) system designed specifically for surgical, health care, or other imaging that provides high-resolution interactive audio, video and data communications between hospital operating room/procedure room environments and other remote locations for education, consulting, surgical assistance, diagnostics, demonstrations, and the like. The mobile VCVP station generally comprises a multi-camera and control system mounted on a mobile platform, the platform including an articulating boom assembly mounted on a wheeled cabinet enclosure, an array of video production equipment inside the cabinet, an array of teleconferencing equipment inside the cabinet, and a fail-safe battery system in the cabinet for powering the foregoing. The articulating boom is fully-pivotable and extendable, and one of the remote control Pan-Tilt-Zoom cameras of the multi-camera and control system are mounted at the end of the boom for overhead images of healthcare procedures. Another remote control Pan-Tilt-Zoom camera is mounted proximate the base of the boom to provide a view of the clinical team or entire operating room. The camera control system includes a full operator console with controls and a plurality of four 4" TFT color monitors for operator previewing. Two full size audience viewing monitors are mounted on the platform to allow a view of the broadcasted video feed and a view of the far side. The outputs from the remote control cameras and other video sources (such as laparoscopes, endoscopes, medical imaging devices and other video sources) are inputted to a video switcher, and then on to both teleconferencing for live interactive broadcast, and as well to the video production equipment which provide the real time capability to make Hard Drive, Mini-DV, S-VHS, VHS and DVD format recordings for the surgeon to leave with if desired. The platform includes a 19" rack-mount cabinet for housing all the video production equipment in a vented environment, as well as a rechargeable battery power supply. The power supply is a dual-battery fed to a power distribution and isolation transformer for independent wireless power. The platform can also be plugged into any AC outlet. The platform is mobile and self-contained and can be moved into any venue.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

The present invention is a mobile communication and video production (VCVP) system designed specifically for surgical imaging that provides high-resolution interactive audio, video and data communications, production and recording capabilities at hospital operating room/procedure room or field environments for transmission to other remote locations for education, consulting, surgical assistance, diagnostics, demonstrations, and the like.

Figure 1:
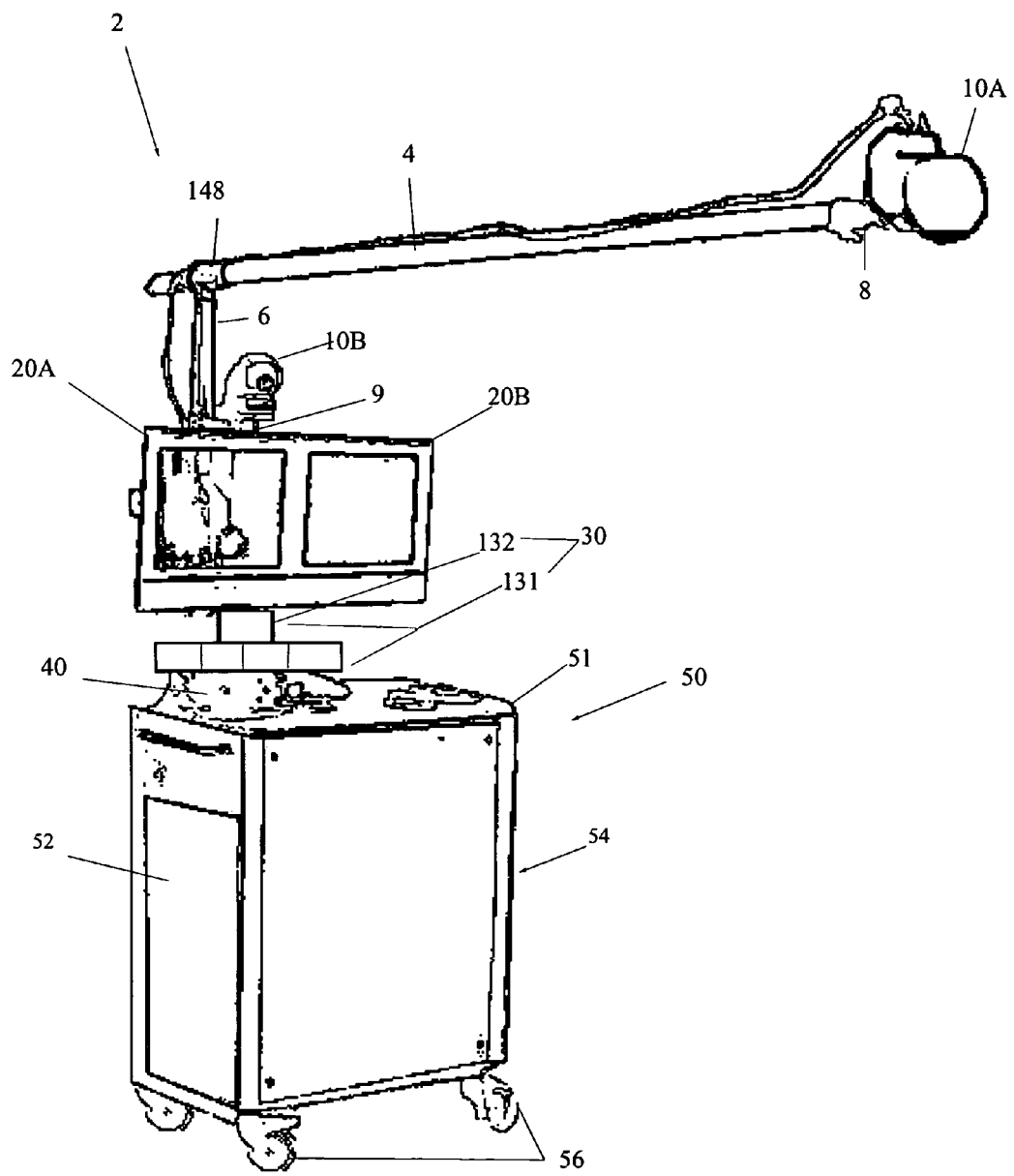
FIG. 1 is a front perspective view of the mobile VCVP station 2 according to the present invention.

FIG. 1 is a front perspective view of the mobile VCVP station 2. Mobile VCVP station 2 generally comprises a multi-camera video and control system (to be described) mounted on a mobile platform 50, an array of video production equipment inside the platform, an array of teleconferencing and networking equipment inside the platform, and a fail-safe battery system in the platform for powering the foregoing.

The platform 50 includes a fully-articulating telescoping boom 4 mounted atop a support mast 6, which is in turn mounted atop a wheeled cabinet. The camera and control system includes a plurality of remote control Pan-Tilt-Zoom cameras (at least two are preferred as in the illustrated embodiment . . . 10A, 10B), one camera of which (10A) is mounted at the end of the boom 4 for overhead images of healthcare procedures. The other remote control Pan-Tilt-Zoom camera 10B is mounted along the mast 6 to provide a full view of the clinical team or entire operating room. Both remote control cameras 10A & 10B are mounted on adjustable camera heads 8, 9, respectively, including quick-release brackets to supplement their inherent remote control pan/tilt/zoom capabilities. Both remote control cameras 10A & 10B are controlled by fixed controls mounted on mobile platform 50 or by wireless remote controls, and their outputs are coupled both to the video production equipment as well as the teleconferencing and networking equipment inside the platform 50. In addition to remote control cameras 10A & 10B, the fixed controls, remote controls, video production equipment and networking equipment in platform 50 are capable of handling additional cameras if desired. Specifically, using the equipment described below the camera and control system may accommodate up to four Pan-Tilt-Zoom cameras. Moreover, the video production and communication equipment inside the platform 50 includes a plurality of auxiliary inputs for connection of external (remote) endoscopes, laparosopes, or other medical imaging devices or remote video cameras as desired to completely capture a given surgical procedure. The system also includes a wireless microphone and wireless receiver/transmitter. This combination of video/audio sources facilitates the complete and unobstructed capture of surgical procedures from multiple selectable angles and proximities, all from a singular point of control.

The mobile VCVP station 2 is designed to be manned and controlled by a single operator (rather then a full production crew as typically required using conventional means), and for this the camera control system includes an operator console with controls 40, and a preview panel 30 comprising a plurality of small color monitors pivotally mounted on the mast 6 for operator previewing. In addition two full size color monitors 20A & 20B are pivotally mounted on the mast 6 above the preview panel 30 to allow previewing by the operator or others and a view of the far side participant(s). The boom 4 and mast 6 stem from a work surface 51 atop the mobile platform 50, beneath which a cabinet enclosure houses an array of video production and teleconferencing equipment to be described. The cabinet enclosure includes two sets of doors 52, 54 for access to a rack-mount support assembly for housing all the video production and communications equipment in a vented dual-column environment overtop the power supply. Generally, the back door 52 provides access to the patch panel, speaker system and power supply, while the front door 54 provides access to video production equipment that provides the real time capability to make recordings to a hard drive, or Mini-DV, S-VHS, VHS and DVD format recordings for the surgeon to leave with if desired, and to and communications (teleconferencing) equipment. The platform 50 is supported on heavy-duty locking castors 56 for mobility.

Figure 2:
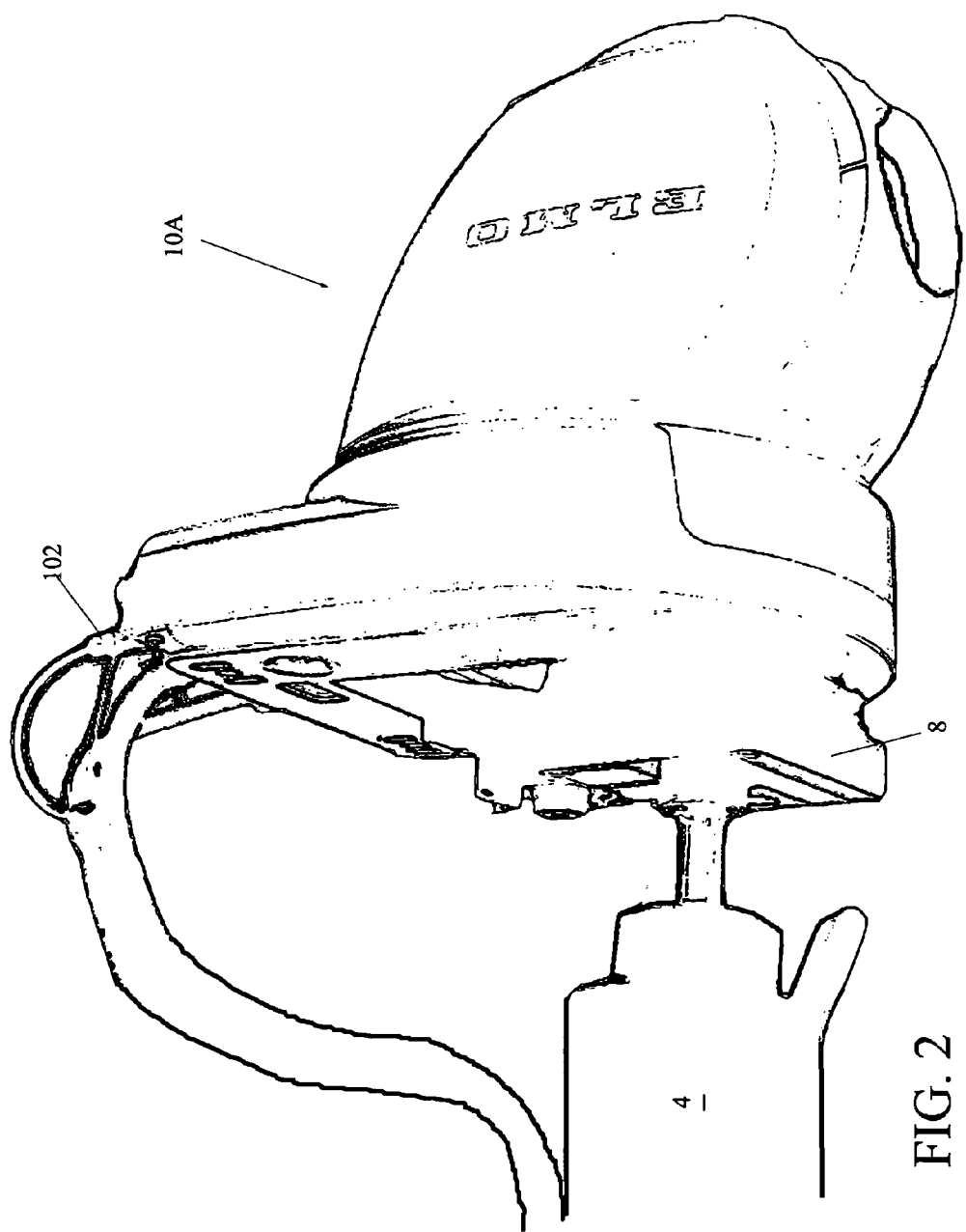
FIG. 2 is a perspective view of camera 10A mounted at the end of the boom 4 for overhead images.

FIG. 2 is a perspective view of camera 10A mounted at the end of the boom 4 for overhead images. Camera 10A is presently a model PC110R1 Elmo video camera mounted on the snap-in receptacle of a professional camera head mount 8. A Bogen Manfrotto® 3262 camera arm wi snap-in receptacle is presently preferred. The camera 10A is connected by conventional cables coupled by a male connector 102, the cables running the length of boom 4. Referring back to FIG. 1, a preferred camera 10B is an Elmo model PC110S which may be pivotally mounted on a yoke bracket compression fit directly on mast 6. If desired, camera 10B may also be mounted on an optional camera head mount 9 although this is not so necessary because camera 10B is primary intended for wide angle viewing. The camera switching and control circuitry (to be described) is capable of controlling as many as four remote control cameras, and so additional cameras may be attached to mast 6 or boom 4 as desired.

Figure 3:
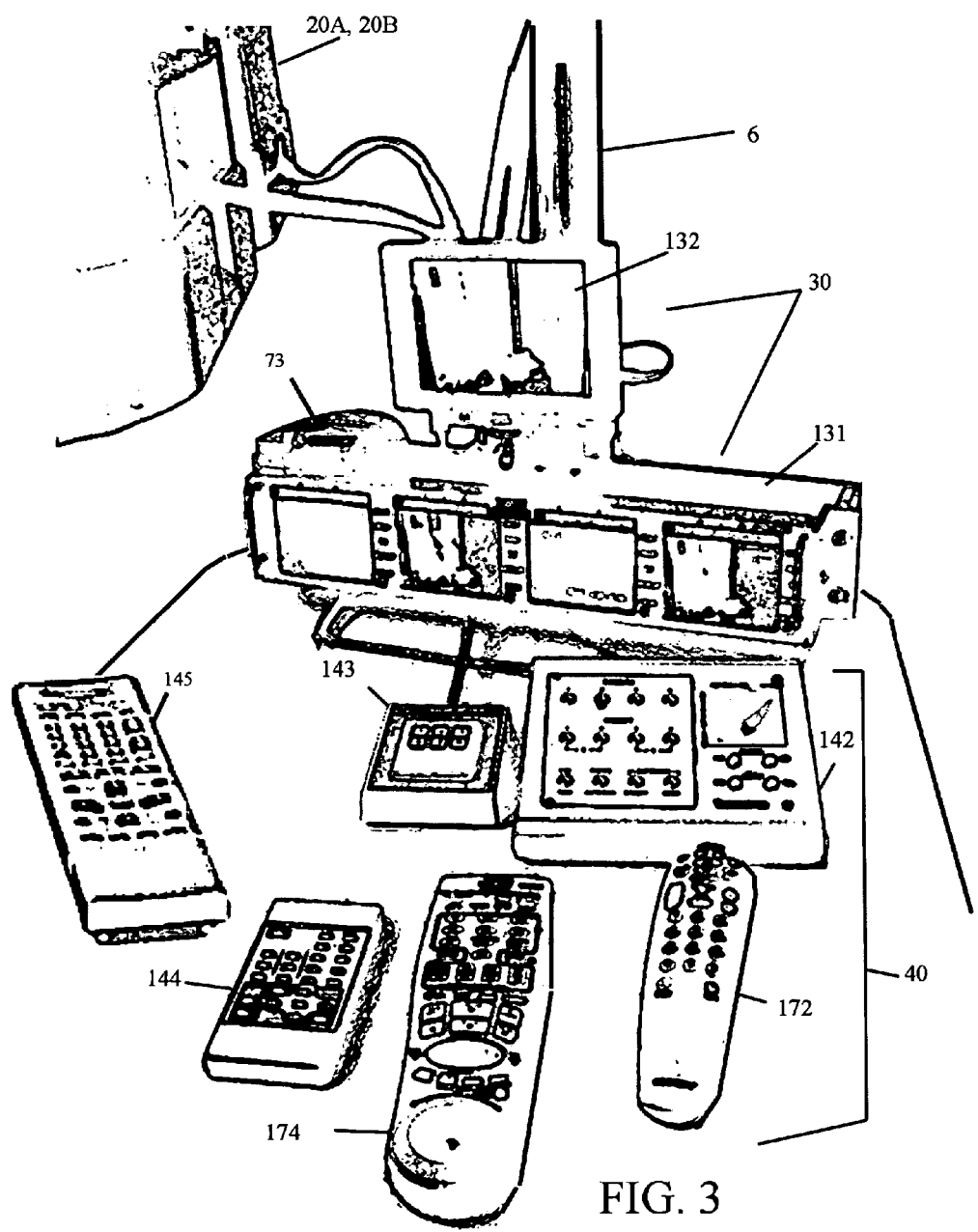
FIG. 3 is a perspective view of the operator console with controls 40, and a preview panel 30.

FIG. 3 is a perspective view of the operator console with controls 40, and a preview panel 30 comprising a plurality (here four) of small color monitors pivotally mounted on the mast 6 for operator previewing. The controls 40 sit atop work surface 51 on the mobile platform 50. The Elmo cameras 10A, 10B described are commonly controlled by a hardwired camera controller 142 which controls the pan/tilt/zoom/focus/iris functions for up to four cameras. A suitable camera controller 142 is the Telemetrics, Inc. Model CP-ITV-VCC-4 with joystick control. Additionally, remote control of the cameras 10A & 10B is possible with a wireless remote controller 144, which may be an infrared camera remote control by Elmo RCW-PTZS. A video switcher keypad 143 provides push-button selection of the active camera (one of up to six in the illustrated embodiment), and provides blinking indicator LEDs designating the currently-active camera. A suitable video switcher keypad 143 is the Extron Model KP-6. Optionally, a video mixer can be used in place of the video switcher keypad 143 to allow fades and transition effects when changing active cameras. Remote control 172 is also provided for the video conferencing codec 86, remote 174 is provided for a combination VHS/MiniDC video tape recorder 72, and remote 145 for a combination optical media recorder 74 (all to be described). These latter remotes 145, 172, 174 are included or optional accessories matched to their respective components.

The preview panel 30 comprises an integrated mini-display panel 131 of small 4" color monitors, one for each of the four possible cameras including 10A & 10B, pivotally mounted on the mast 6 for operator previewing. A suitable mini-display panel 131 is a 4×4" TFT LCD panel by Tote Vision, Inc., Seattle, Wash., model 4-amp LCD. The mini-display panel 131 is mounted on a display bracket attached by a yoke compression fitting to the mast 6. Preview panel 30 also includes an active broadcast monitor 132, preferably a larger TFT LCD for displaying the video from the currently-active (selected) camera. A suitable active broadcast monitor 132 is a 6.4" TFT LCD, Model LCD-640 by Tote Vision, Inc. The active broadcast monitor 132 is likewise mounted on a display bracket attached by a yoke compression fitting to the mast 6, just above the mini-display panel 131.

In addition to the operator console with controls 40, two viewing monitors 20A, 20B are likewise attached by a bracket and yoke compression fitting to the mast 6, just above the active broadcast monitor 132, these two main monitors allow the immediate surgical team to view the audience on the far side of a teleconference, as well as the video feed being broadcasted to that audience. Suitable viewing displays 20A, 20B are Panasonic Model TC1701 17" diagonal LCD TVs held together on a single adjustable bracket.

Figure 4:
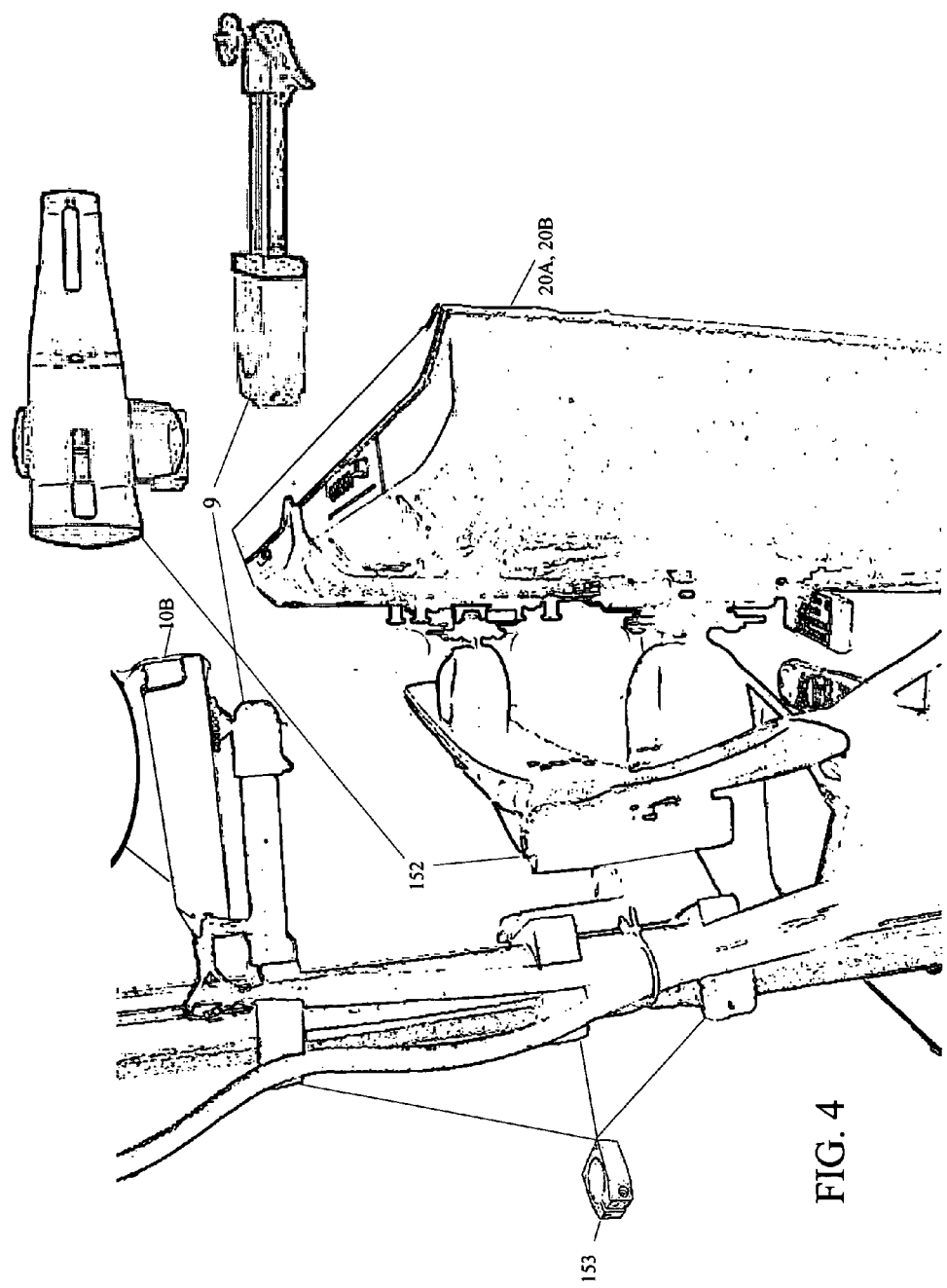
FIG. 4 is a close-up view showing the brackets 152, 154 for attaching the two viewing monitors 20A, 20B as well as camera 10B to the mast 6, respectively.

FIG. 4 is a close-up view showing the bracket 152 for attaching the two viewing displays 20A, 20B to the mast 6. Bracket 152 spans both displays 20A, 20B with an outstretched crossbar that secures the displays 20A, 20B at the sides. The camera head 9 for mounting camera 10B to the mast 6 is also shown. Bracket 152, camera head 9 and mini-display panel 131 (all other fixtures to mast 6) are made using yoke compression fittings 153 which grip the mast 6, all of the yoke compression fittings 153 being substantially uniform. Each yoke compression fitting 153 is an aluminum collars that is hex-screwed together around the mast 6 to anchor the respective components to the mast.

Figure 5:
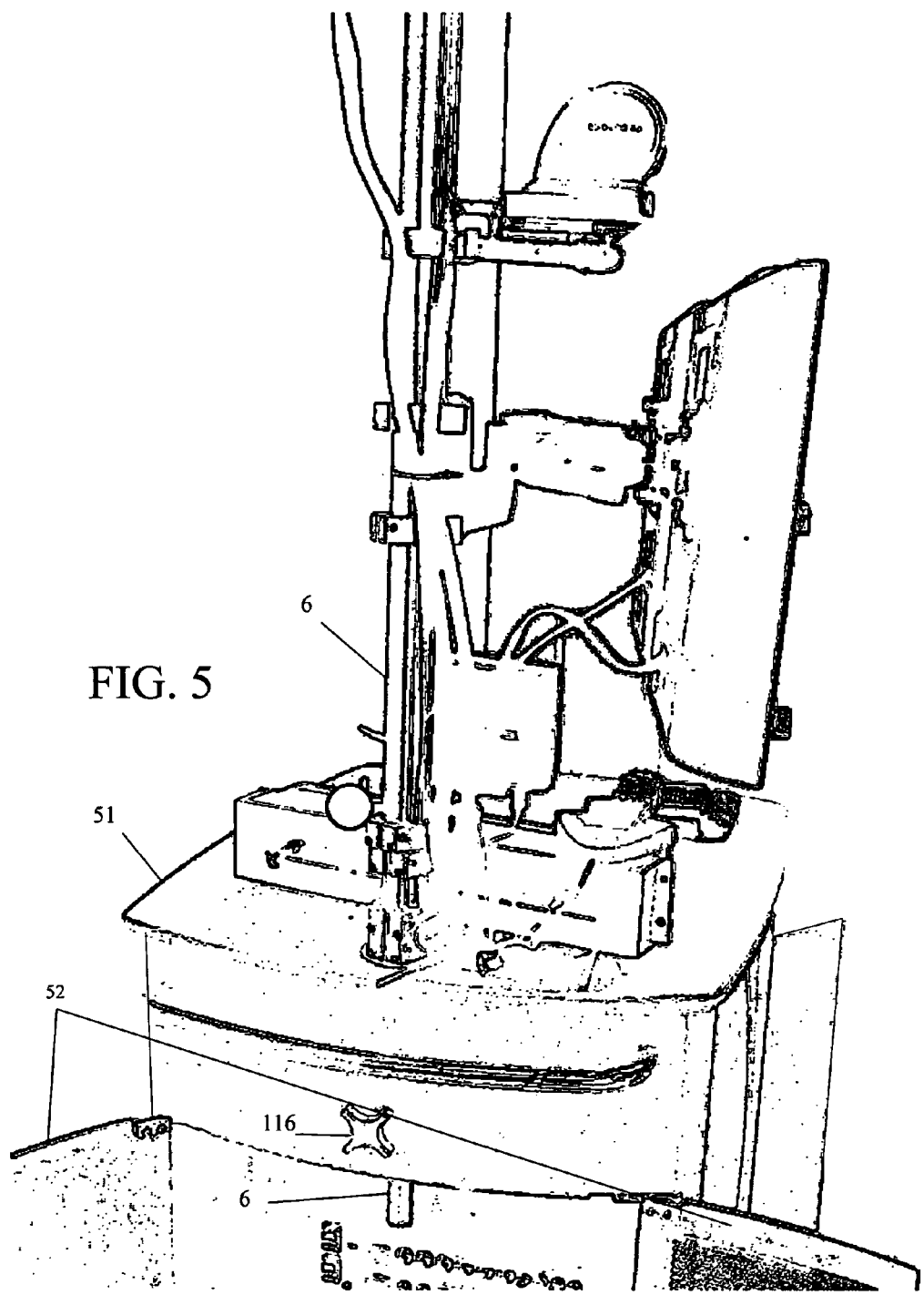
FIG. 5 is a side view of the mobile VCVP station 2 with open back door 52 to reveal the mast 6 configuration.

FIG. 5 is a side view of the mobile VCVP station 2 with open back door 52 to reveal the mast 6 configuration. The mast 6 is a height adjustable 2" diameter stainless steel tube that penetrates the work surface 51 through a pre-cut hole therein. The mast 6 is slidably supported in a yoke inside the mobile platform 50, and is locked at a fixed vertical position by lock knob 116. Referring back to FIG. 1, the boom 4 comprises three telescoping sections of aluminum tubing which telescope from approximately 5 to 15'. The boom 4 is horizontally attached to mast 6 at a T-junction 148 which preferably includes a Teflon collar-insert in its upper extent which serves as a bushing to allow easy sliding deployment.

To assemble the mobile VCVP station 2, a user will first slide the mast 6 into the pre-cut hole in surface 51 and into the yoke inside the mobile platform 50, where it is locked at a fixed vertical position by lock knob 116. The mini-display panel 131 is then secured to the mast via a yoke collar 153. The active broadcast monitor 132 is then secured to the mast via a yoke collar 153. The dual viewing displays 20A, 20B are then secured to the mast via two yoke collars 53 and bracket 152. The mast camera mount 9 is secured to the mast 6 by a yoke collar 53, and the Elmo camera 10B is secured thereto by quick-release plate. Next, the T-junction 148 is slidably inserted onto the top of the mast 6. The boom 4 is inserted into the T-junction 148. The Elmo camera mount 8 is secured to the boom 4, and the Elmo camera 10B is attached and secured to the boom 4 (likewise by quick-release plate). All electrical components are then wired-up, and all wires are labeled to expedite this. The wiring connections are described in detail with regard to FIG. 8. The system 2 is now fully assembled.

In use, the mobile VCVP station 2 is wheeled and parked (by locking castors 56) at a convenient unobtrusive location in an operating room or other environment. The mast 6 is pivoted to angularly position the boom 4 as desired, and the telescoping boom 4 is extended to position the camera 10A directly overhead the operating site. Likewise, camera 10B is adjusted to give a full view of the surgery. These adjustments are further facilitated by positioning the camera heads mounts 8, 9. With cameras in place, the operator pivots his preview panel 30 over the controls 40, and pivots the two full size color monitors 20A & 20B to provide the surgical team or other onlookers with preview capability. As the surgery proceeds, the operator can multiplex the camera signals and produce a live high resolution video and audio feed that is networked in real time for teleconferencing, and/or recorded in any known format such as Hard Drive, Mini-DV, S-VHS, VHS and DVD. All of the foregoing is powered by the internal dual-battery supply, making the platform completely mobile and self-contained such that it can be repositioned in any venue.

Each time the system 2 is rolled from one location to another it is imperative to remove the video and power cables from the boom camera 10A, remove the boom camera 10A from boom 4, remove boom 4 from T-junction 148, and lower the mast 6 to clear any doorway. Once the system 2 is in its new location, the castor wheels 56 should be locked.

Figure 6:
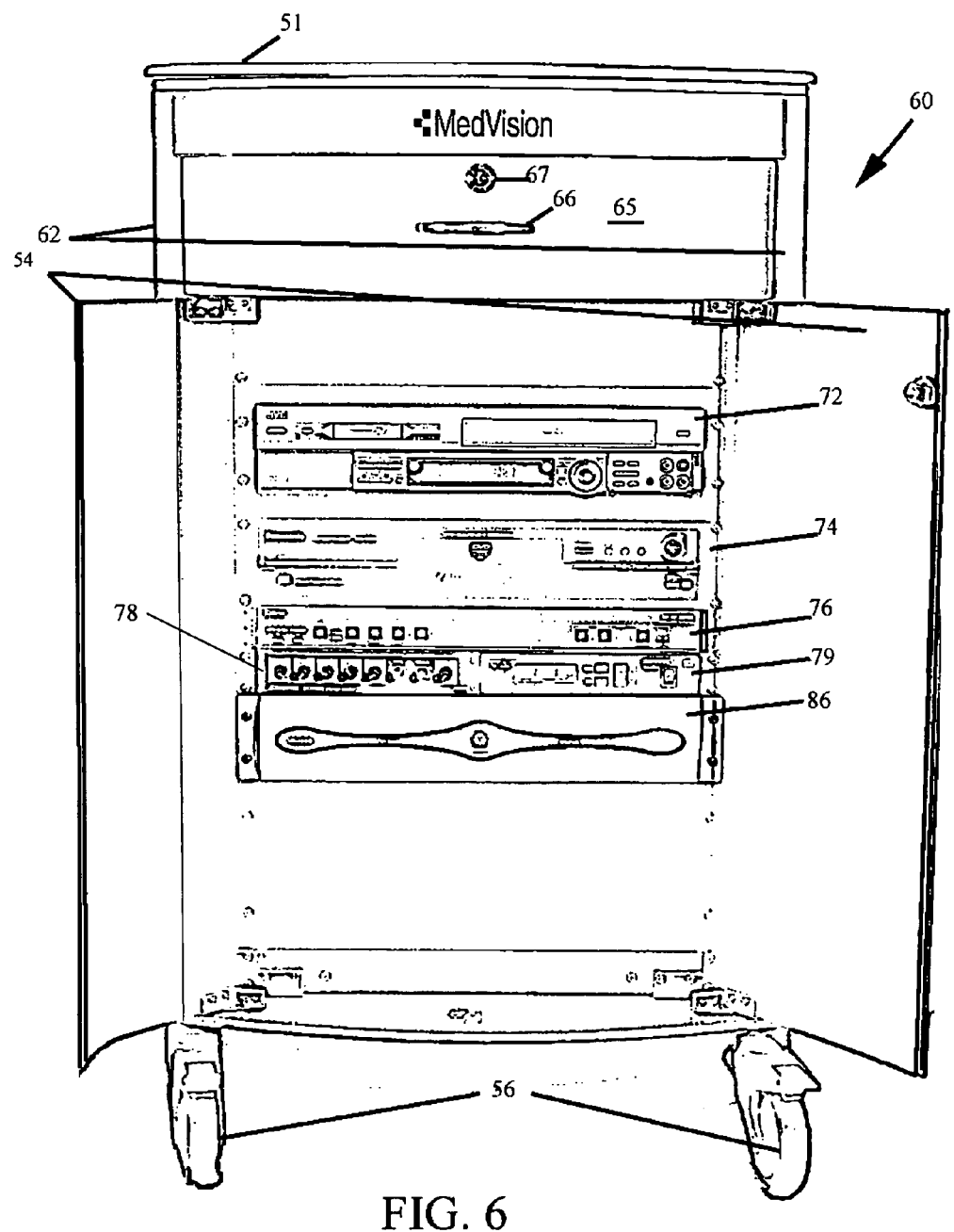
FIG. 6 is a front view of the mobile platform with open front door 54 to provide access to video production and communications equipment.

FIG. 6 is a front view of the mobile platform with open front doors 54 providing access to video production equipment that provides the real time capability to record to a hard drive, or make Mini-DV, S-VHS, VHS and DVD format recordings for the surgeon to leave with if desired, and to communications (teleconferencing) equipment. The work surface 51 sits atop the mobile platform 50, beneath which a cabinet enclosure 60 houses an array of video production and teleconferencing equipment. Platform 50 is supported on heavy-duty locking castors 56 for mobility. The cabinet enclosure 60 is a heavy duty reinforced vented enclosure formed by four tubular aluminum corner struts 62 which span the work surface 51 to an aluminum bottom panel. Both front and back of the cabinet enclosure 60 are formed with a shallow arc for aesthetics. The front doors 54 comprise Lexan™ hinged panels with standard keylocks, while back doors 52 comprise a pair of conforming aluminum panels with standard keylocks. The side panels comprise Plexiglass™ panels which are attached between the aluminum corner struts 62. The work surface 51 comprises a Corian™ countertop. A rack-mount support framework is installed in the interior of the cabinet enclosure 60 to support the components, the rack-mount support framework subdividing the interior into front and back sections generally allowing access to video production and communications equipment through the open front door 54, and to patch panel, speaker system and power equipment through the open back door 52. A slidable drawer 65 with handle 66 and lock 67 is provided above the front doors 52 for storage of the remote controls, media, etc. The video production equipment visible in FIG. 6 includes (from top) a combination VHS/Mini-DV recorder 72, an optical media recorder 74, a video switcher 76 with video-conferencing capability, a sound mixer 78, a wireless microphone receiver 79, a video conferencing codec 86, and a computer hard drive 89 (obscured) that is mounted behind the accessible components. A suitable combination video tape recorder 72 is the JVC Super-VHS ET Professional video series with mini-DV and VHS record/playback capabilities. A suitable combination optical media recorder 74 is a Panasonic DMR-T3030 with DV-RAM and DVR record/playback capabilities. A suitable video switcher 76 is the Extron SW-6 AV Series video switcher. This particular unit is a six input, two output video (NTSC/PAL/SECAM) switcher with vertical interval switching ability. The SW-6AV is capable of switching up to six independent composite video (line video) sources to one video stream out (split into two independently buffered outputs, an S-video and composite). In addition to a rear panel (9-pin) RS-232/contact closure control port, the SW-4AV includes sync in/out BNC connectors to provide "seamless" vertical interval switching from an external sync source. The preferred version is an auto-switch version that automatically switches to the desired input source once an active input signal is detected, a helpful feature four auto-selection of the active one of the six video inputs including cameras 10A & 10B. A suitable sound mixer 78 is the Shure SCM 262 stereo mixer for mixing microphone and stereo inputs. This unit is capable of mixing two active balanced XLR microphone input channels and three stereo input channels. A suitable wireless microphone system 79 is the Shure ULX-S4 which provides 1400 selectable, pre-programmed frequencies and Automatic Frequency Selection to ensure a clear channel. This unit works with commercially-available Shure microphone transmitters typically worn by the surgeons. A suitable video conferencing codec 86 is the VS 4000 video conferencing codec by Polycom, Inc., which includes a remote control unit 172 (shown in FIG. 3) for remote dialing, volume control, etc. The remote control unit 172 communicates with codec 86 through an infrared receiver 73 shown atop the work surface 51 and which is connected to codec 86. Tandberg manufactures another video conferencing codec which is equally suited for use as codec 86 (the Tandberg 6000), and Sony also supplies suitable codecs. A suitable computer hard drive 89 (obscured) is a Seagate® 180 Mb external IEEE 1394 firewire hard drive.

Referring back to FIG. 3, the operator controls 40 include the remote control 174 for the combination VHS/Mini DV recorder 72, remote 145 for the optical media recorder 74, remote control 172 for the video conferencing codec 86, plus the wired controller 142 and the wireless remote control 144 for cameras 10A & 10B. Remotes 145, 174 and 172 are standard remotes that are either provided with or supplied as optional accessories for their corresponding above-described components. The Elmo remote control unit 144 is not and must be programmed for proper operation by supplying ID numbers for the cameras. This is done by turning ON each camera to be set with an ID No., while leaving other adjacent cameras in the OFF position. The remote 144 is then set with a remote ID No. for the ON camera. This is repeated for all other cameras in the same way. Once programmed as such, all pan/tilt/zoom cameras can be operated selectively by pressing the respective ID button on remote 144. Only the elected camera can then be operated via the wireless remote controller. In the illustrated embodiment the pole camera 10A can only be controlled by the wired remote control 142, while the boom camera 10B can be operated by either the infrared remote control 144 or the wired remote control unit 142.

The wired Telemetrics remote control unit 142 includes a manual joystick to move the selected camera in any direction. Both remotes 142, 144 allow control over camera Pan/Tilt, Zoom, Focus, and IRIS (bright or dark).

Figure 7:
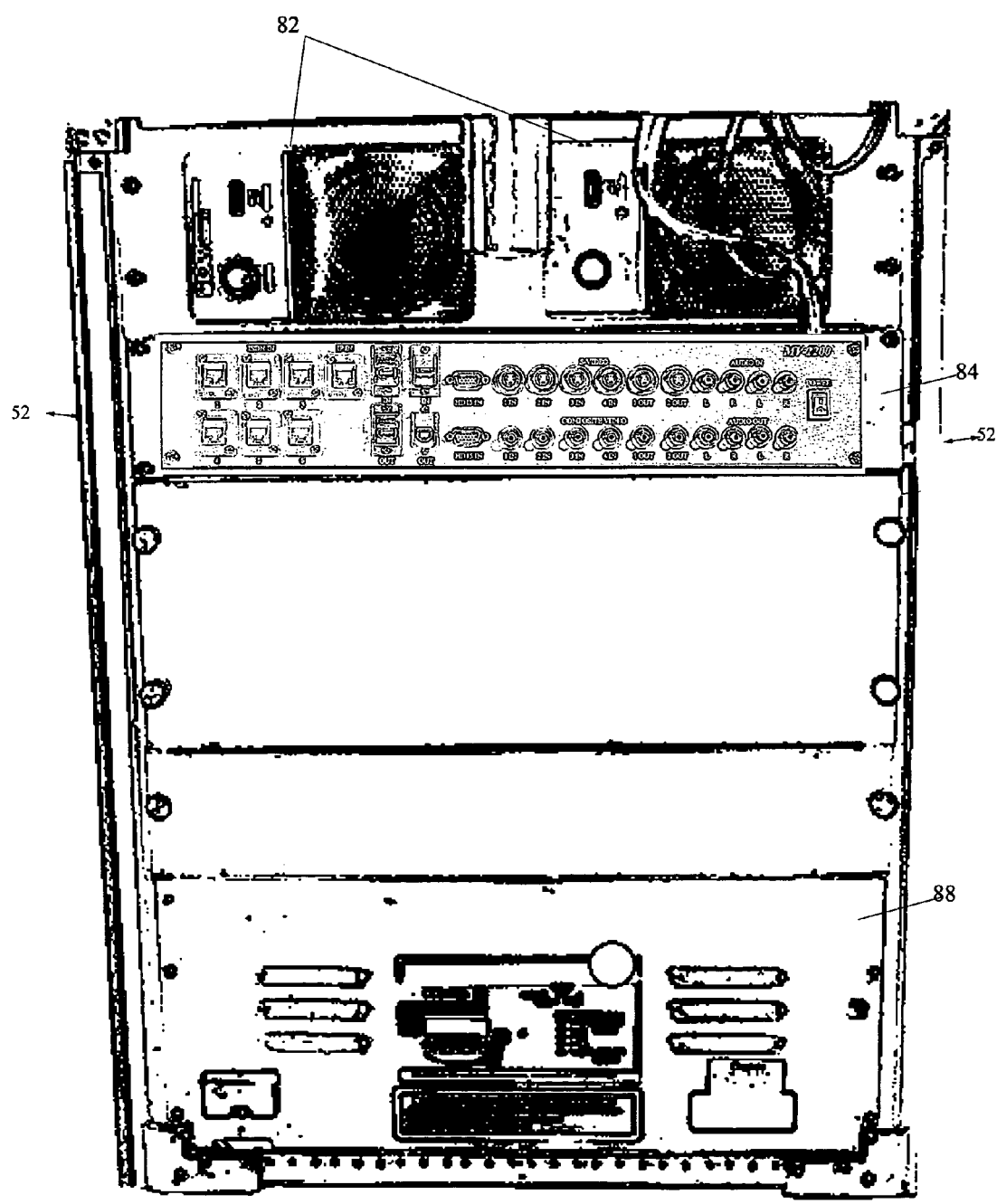
FIG. 7 is a rear view of the mobile platform with open back door 52 to provides access to the patch panel, speaker system and power supply.

FIG. 7 is a rear view of the mobile platform with open back door 52 providing access to the patch panel, speaker system and power source. A panel is provided above the back doors 52 behind which the mast 6 is slidably mounted. The networking and teleconferencing equipment visible in FIG. 7 includes (from top) a powered speaker system 82, a video patch panel and patch panel 84 that serves as the central connection interface for the other components, and rechargeable battery power supply equipment 88. A suitable powered speaker system 82 is a Fostex 6301B personal monitor self-powered speaker pair. A suitable patch panel 84 is the 84MV-2200 Patch Panel wi 6 ISDN input ports, one IP input port, 2 USB ports, one firewire in/out port, one RS-232C port, 6 S-video (4-in 2 out) and a like number of composite video ports, two pair of stereo audio ports (one in and one out), and a power switch.

Figure 8:
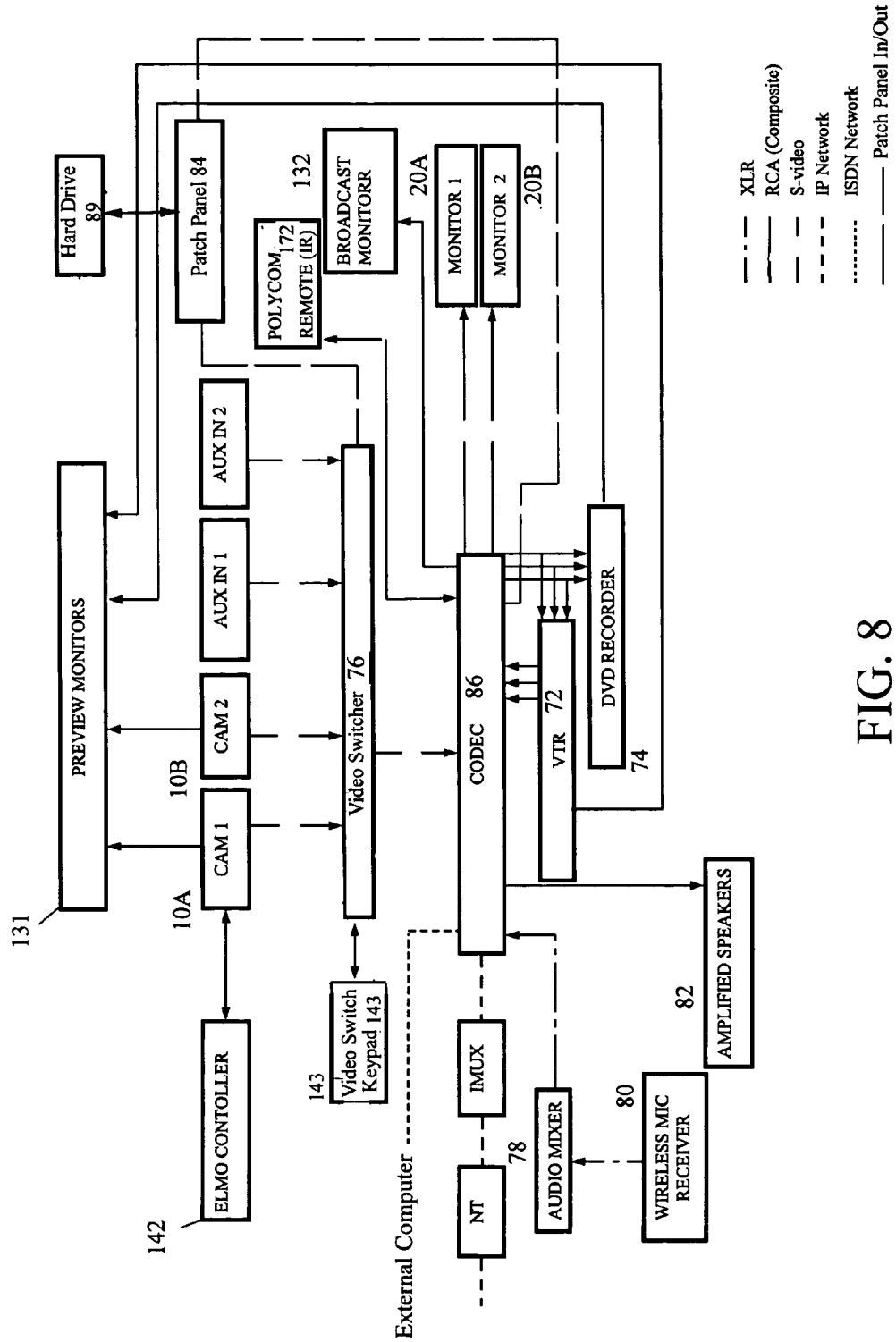
FIG. 8 is a schematic diagram showing the audio, video, and network interconnections of the above-described components.

FIG. 8 is a schematic diagram showing the audio and video component and remote (infrared) interconnections of all the above-described components. Patch panel 84 is the primary pass-through interface for the component interconnections and includes the necessary input/output ports as described above for flexible connections using the appropriate cabling. The remote video switcher keypad 143 is connected to and controls the video switcher 76, which is in turn connected through patch panel 84 to each of the cameras 10A & 10B, as well as the two auxiliary camera inputs (for endoscope, laparoscope, other medical imaging device, etc.). Thus, the pan/tilt/zoom/focus functions for cameras 10A & 10B are controlled by the remote video switch control 143. Video switcher 76 is then connected through patch panel 84 to codec 86. The video switcher keypad 143 through video switcher 76 selects the active camera to feed the main video signal through to codec 86.

Codec 86 is connected to the patch panel 84 as well, and the codec 86 S-video outputs are connected to monitors 20A & 20B and to the broadcast monitor 132 for viewing.

The computer hard drive 89 is also connected (by firewire) through patch panel 84 to the codec 86 for recording, and any external computer or laptop my be connected to the codec 86 for controlling the hard drive 89 or for downloading still pictures or the like.

The wireless microphone receiver 79 is connected to sound mixer 78, which in turn is connected to the audio input ports of the codec 86.

The inputs to each of the recording components of the video/audio production equipment (video tape recorder 72 and optical recorder 74 are connected to a respective codec 86 audio/video output, and the outputs run to preview panel 131. The speakers 82 are connected to the audio outputs of the codec 86.

The rechargeable battery power supply equipment 88 is connected to and powers each of the above-described components.

Figure 9:
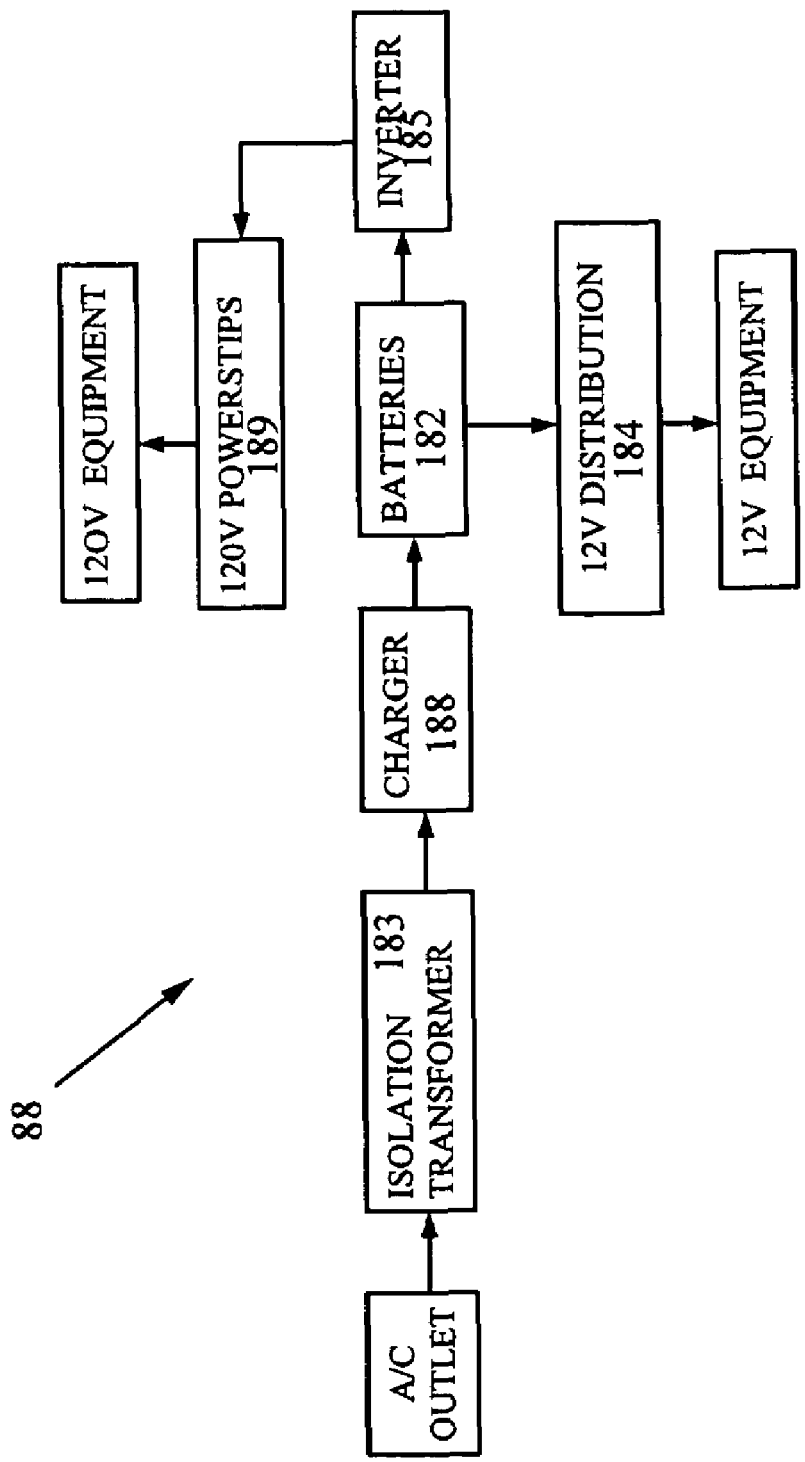
FIG. 9 is a schematic diagram of the battery power system 88.

The battery power system 88 is installed in the rack mount supports holding the above-described components. FIG. 9 is a schematic diagram of a presently-preferred battery power system 88, which includes two safety-sealed AGM™ 12 volt lead-acid batteries 182 behind a combination regulated power supply/battery charger 188. The power input to battery charger 188 is connected to a standard isolation transformer 183 (for surge protection) to a standard wall outlet. A suitable power supply/charger 188 is the Intella Model PCS-2201 trickle charger. The batteries 182 are safety sealed to prevent leakage in a surgical environment. The batteries 182 are also connected to a conventional 12 vdc distribution panel for coupling all 12 vdc equipment described above. In addition, the batteries 182 are connected through a conventional 120 vac power inverter 185 for AC conversion, which in turn is connected to an AC power strip 189 for coupling all 120 vac equipment described above.

It is noteworthy that the regulated power supply/battery charger 188 and power inverter 185 can be combined in a single device (combination regulated power supply/battery charger/power inverters being readily available). In this instance the power-strips 189 are connected directly to the combination regulated power supply/battery charger/power inverter.

To use the system 2 in real time for teleconferencing, the video conferencing codec 86 must be programmed and networked in accordance with the manufacturer instructions (e.g., Polycom, Inc.).

During installation a technician will program the video conferencing codec 86 to operate in the particular IT environment as necessary, inclusive of all network info. This is done by a display screen on the codec 86. A graphical menu allows the user to set the following parameters.

WINS Resolution—allows codec 86 to be resolved to an IP address in a routed environment. When this option is selected, the codec 86 sends requests to the WINS server for WINS name resolution.

DHCP—The Dynamic Host Configuration Protocol allows a server to dynamically assign IP addresses to devices on a LAN. The DHCP option can be set to Off, Client, or Server. When Off is selected, the IP address, DNS servers, default gateway, subnet mask, and WINS server information must be entered as static addresses. These addresses are permanent until they are manually changed. When the Client option is selected, the user's DHCP server automatically assigns an IP address, a DNS server address, a default gateway, a subnet mask, and a WINS server address. When Server is enabled, the options IP Address, DNS Servers, Default Gateway, Subnet Mask, and WINS Server cannot be changed.

DNS Servers—DNS servers are computers which translate domain names (example: ww.polycom.com) into IP addresses. If the DHCP Client option is selected, the DNS server addresses are automatically filled in and you cannot make any change to this field. If the DHCP Off option is selected, the DNS server addresses must be entered manually.

Default Gateway—The default Gateway is a router on the local network. Its main task it to act as an interpreter between two systems that do not use the same communications protocol, data formatting, and other network functions. Your system must go through this router to access destinations outside of its network.

If the DHCP Client option is selected, the Default Gateway address is automatically filled in. If the DHCP Off option is selected, the Default Gateway address must be entered manually.

Subnet Mask—A subnet mask is a number that identifies a subnetwork so that an IP address can be shared on a local network. If the DHCP Client option is selected, the subnet mask address is automatically filled in. If the DHCP Off option is selected, the address must be entered manually.

WINS Server—This is a Windows NT computer that resolves computer names to IP addresses in a routed environment.

The codec 86 is also capable of making an ISDN call.

The mobile VCVP station 2 set forth above is specifically designed for surgical imaging and is suitable for operation by a single trained operator, replacing the traditional team of videographers. It does this by offering a complete array of audio and high-resolution video capture tools, mixing and editing tools, recording capabilities to a variety of common analog and digital formats, and real time video and data communications capabilities for networked communications for teleconferencing between hospital operating room/procedure room environments and other remote locations for education, consulting, surgical assistance, diagnostics, demonstrations, and the like.

Moreover, the mobile VCVP station 2 has a footprint well-suited for a hospital environment because all components are contained in an aesthetically-pleasing base cabinet, the base is portable for use in all the operating rooms in a given hospital, and the fully-articulating boom-mounted video camera gives high-resolution close-up surgical imaging, and the sealed fail-safe battery system exceeds UL specifications for battery-operated surgical devices. The array of components in the cabinet facilitate full mixing, editing and production capabilities, plus full teleconferencing and networking capabilities.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

We claim:

1. A mobile videoimaging station, comprising:
a wheeled cabinet;

a height-adjustable and length-adjustable camera support comprising a mast mounted to and extending upward from said cabinet, and a telescoping boom pivotally mounted at one end to said mast;

a first video camera having remotely controlled pan, tilt and zoom functions mounted distally on another end of said boom;

a second video camera mounted on said mast;

controls mounted on said wheeled cabinet for remotely controlling the pan, tilt and zoom functions of said first video camera;

a plurality of displays for displaying outputs from said first video camera and said second video camera;

a video production system including a switch for compiling a single video feed from said first video camera and said second video camera; and a teleconferencing system for network conferencing of said video feed in real time;

a power supply mounted inside the cabinet;

whereby said videoimaging station may be controlled by a single operator to produce said video feed.

2. The mobile videoimaging station according to claim 1, wherein said plurality of video displays comprises a mini-display panel including a plurality of displays for displaying outputs from the first video camera and the second video camera to an operator.

3. The mobile videoimaging station according to claim 2, wherein said plurality of video displays further comprises an active broadcast preview monitor for displaying the live video feed compiled from said first video camera and said second video camera to onlookers.

4. The mobile videoimaging station according to claim 1, wherein said teleconferencing system comprises a codec for networked videoconferencing.

5. The mobile videoimaging station according to claim 4, wherein said video production system comprises a VHS/Mini-DV recorder for recording said video feed.

6. The mobile videoimaging station according to claim 5, wherein said video production system comprises an optical media recorder for recording said video feed.

7. The mobile videoimaging station according to claim 1, wherein said power supply comprises a rechargeable battery power supply.

8. A mobile videoimaging station, comprising:
a wheeled cabinet having a work surface;
a height-adjustable mast extending vertically from the work surface of said cabinet;
a length-adjustable boom extending from said mast;
a plurality of remotely-controlled video cameras, including at least one said camera having remotely controlled pan, tilt and zoom functions mounted distally on one end of said boom;
controls mounted on the work surface of said mobile platform for remotely controlling the pan, tilt and zoom functions of said at least one camera;
a video production system mounted inside the cabinet for mixing, producing and recording a single video feed from said plurality of cameras; and
a teleconferencing system mounted inside the cabinet for network conferencing of said video production in real time; a rechargeable battery power supply;
whereby said mobile video communications and video production station may be wheeled into a convenient location in an operating room or other environment and controlled by a single operator to produce said video feed.

9. The mobile videoimaging station according to claim 8, wherein said video production system comprises a mini-display panel including a plurality of displays for displaying outputs from the at least one remotely-controlled video camera to an operator.

10. The mobile videoimaging station according to claim 9, wherein said video production system comprises an active broadcast monitor for displaying the live video feed compiled from said at least one remotely-controlled video camera to an operator.

11. The mobile videoimaging station according to claim 9, wherein said video production system comprises at least one display for displaying outputs from the at least one remotely-controlled video camera to onlookers.

12. The mobile videoimaging station according to claim 8, wherein said, teleconferencing system comprises a codec for networked videoconferencing.

13. The mobile videoimaging station according to claim 12, wherein said video production system comprises a video tape recorder for recording said video feed.

14. The mobile videoimaging station according to claim 13, wherein said video production system comprises an optical media recorder for recording said video feed.

15. The mobile videoimaging station according to claim 8, wherein said rechargeable battery power supply comprises a pair of rechargeable batteries for failsafe power.

* * * * *